United States Patent  (10) Patent No.: US 9,604,005 B2
Stockmar  (45) Date of Patent: Mar. 28, 2017

(54) DEVICE FOR INJECTING A MEDIUM INTO OR UNDER THE SKIN WITH A SERIES OF PRESSURE PULSES

(71) Applicant: Jürgen Stockmar, Vienna (AT)

(72) Inventor: Jürgen Stockmar, Vienna (AT)

(*) Notice: Subject to any disclaimer, the term of this patent is extended or adjusted under 35 U.S.C. 154(b) by 365 days.

(21) Appl. No.: 14/052,568

(22) Filed: Oct. 11, 2013

(65) Prior Publication Data

US 2014/0039394 A1    Feb. 6, 2014

Related U.S. Application Data

(63) Continuation of application No. PCT/EP2012/001620, filed on Apr. 13, 2012.

(30) Foreign Application Priority Data

Apr. 13, 2011  (DE) .................. 10 2011 007 314

(51) Int. Cl.
*A61M 5/30* (2006.01)
*A61M 5/48* (2006.01)

(52) U.S. Cl.
CPC ........... *A61M 5/3007* (2013.01); *A61M 5/30* (2013.01); *A61M 5/484* (2013.01)

(58) Field of Classification Search
CPC ........ A61M 11/00; A61M 11/02; A61M 5/30; A61M 5/3007; A61M 5/484; A61M 3/0258
See application file for complete search history.

(56) References Cited

U.S. PATENT DOCUMENTS

| 5,836,909 A  * | 11/1998 | Cosmescu ............ A61B 18/14 600/108 |
| 7,029,457 B2 * | 4/2006 | Rogatchev ............ A61M 5/30 604/131 |
| 2002/0116021 A1 | 8/2002 | Gordon |
| 2004/0097889 A1* | 5/2004 | Pedersen ............ A61M 3/0275 604/264 |
| 2004/0260234 A1* | 12/2004 | Srinivasan ............ A61M 5/30 604/66 |

(Continued)

FOREIGN PATENT DOCUMENTS

| DE | 19607922 A1 | 9/1997 |
| WO | WO 03/037408 A1 | 5/2003 |

(Continued)

OTHER PUBLICATIONS

International Search Report dated Aug. 29, 2012 for International Application No. PCT/EP2012/001620, with English Translation, 7 pages.

*Primary Examiner* — Theodore Stigell
*Assistant Examiner* — Benjamin Koo
(74) *Attorney, Agent, or Firm* — Kilpatrick Townsend & Stockton

(57) ABSTRACT

The invention relates to a device for injecting a medium into or underneath the skin with a series of pressure pulses. The device includes a reservoir (1) for the medium, an application unit (10) to inject the medium into or under the skin, a hydraulic high-pressure pump (6) to pump the medium out of the reservoir (1) into the applicator unit (10), and an electronic control unit (11) that is suitable for regulating the applicator unit (10) such that the medium is injected with a series of pressure pulses into or underneath the skin.

13 Claims, 3 Drawing Sheets

(56) References Cited

U.S. PATENT DOCUMENTS

2010/0016827 A1\* 1/2010 Hunter .................. A61M 5/30
604/500
2010/0072301 A1\* 3/2010 Cater .................. A61M 11/007
239/333

FOREIGN PATENT DOCUMENTS

| WO | 2004/093818 A2 | 11/2004 |
| WO | 2006/086719 A1 | 8/2006 |
| WO | 2010/115499 A1 | 10/2010 |

\* cited by examiner

DEVICE FOR INJECTING A MEDIUM INTO OR UNDER THE SKIN WITH A SERIES OF PRESSURE PULSES

CROSS-REFERENCES TO RELATED APPLICATIONS

This application is a continuation of International Application Number PCT/EP2012/001620, filed on Apr. 13, 2012, which claims the benefit of German Application Number DE 10 2011 007 314.0, filed on Apr. 13, 2011, the entirety of both of which are hereby incorporated by reference herein.

BACKGROUND OF THE INVENTION

The invention relates to a device for injecting a medium into or under the skin with a series of pressure pulses.

DETAILED DESCRIPTION OF THE INVENTION

In medical applications, direct injecting of media into skin under pressure without injection needles is known and utilized, for example, for certain vaccinations. These injections place media, such as, for example medications, under the skin using a single high-pressure pulse.

The object of the invention is to provide a device that injects pressurized media into or underneath the skin with a series of pressure pulses instead of with a single high-pressure pulse.

This object is achieved by the device according to Claim 1. Advantageous embodiments can be found in the dependent claims.

The device according to Claim 1 comprises a reservoir for the medium, an applicator unit to inject the medium into or underneath the skin, a hydraulic high-pressure pump configured to pump the medium out of the reservoir into the applicator unit, and an electronic control unit that is suitable to regulate the applicator unit such that the medium is injected with a series of pressure pulses into or underneath the skin.

The invention makes the transdermal placement of preferably liquid media into or underneath the skin with a series of pressure pulses possible. This allows media, preferably medications, to be placed extensively over a defined area into or underneath the skin with minimal lesions and without the previously required multiple punctures from injection needles. The interruptions during the series of pressure pulses ensure that the stream of liquid medium does not cause any cutting injuries ("water jet cutter" injuries).

The length of a series of pressure pulses can be from a few milliseconds to a few seconds. The device described herein enables the transdermal application of liquid media having a wide viscosity range. The liquid media can represent the substance itself (e.g. hyaluronic acid gel, botulinum toxin, or the patient's own fat), an active ingredient in solution, as a mixture, or can contain the active ingredient undissolved as (nano)particles. The particle can also be an implant. After reaching the target tissue, the media deliver the active ingredient or ingredients to the organism according to the solubility coefficient in bodily fluids. Thus, a so-called controlled release system can be established.

The electronic control unit can additionally be suitable for controlling the hydraulic high-pressure pump and one or more pressure valves and/or pressure limiters such that the medium is injected into or underneath the skin at selectable pressures. Regulation of the system pressure means that the constant starting pressure can be set as desired, and regulation of the applicator unit defines the series of pressure pulses. A line for feeding in the medium from the high-pressure pump to the applicator unit can be simultaneously used as a pressure reservoir and/or to balance out pressure peaks for hydraulic oscillation smoothing, which will reduce the number of components required in the device. The applicator unit can comprise at least one injection nozzle with a nozzle needle 17 that can be opened and closed mechanically/hydraulically, electrically, or piezo-electrically.

Injection of the medium into or underneath the skin can be very flexibly controlled. First, the injection frequency and thus the quantity of medium injected per unit of time can be controlled via the electronic control unit. Second, the injection pressure and thus the injection depth of the medium into or underneath the skin can be controlled via the pressure control valve and pressure limiter. Third, the deepest possible or the broadest possible injection of the medium into or underneath the skin can be achieved via the shape of the injection nozzle on the applicator unit. Fourth, the quantity of medium to be applied per area can be controlled via the selection of replaceable applicator units and/or the injection nozzles with various diameters. The control can take place via control button(s) on the handle and/or a foot switch.

In the following, the invention is explained by means of advantageous embodiments with reference to the enclosed drawings.

Figure 1:
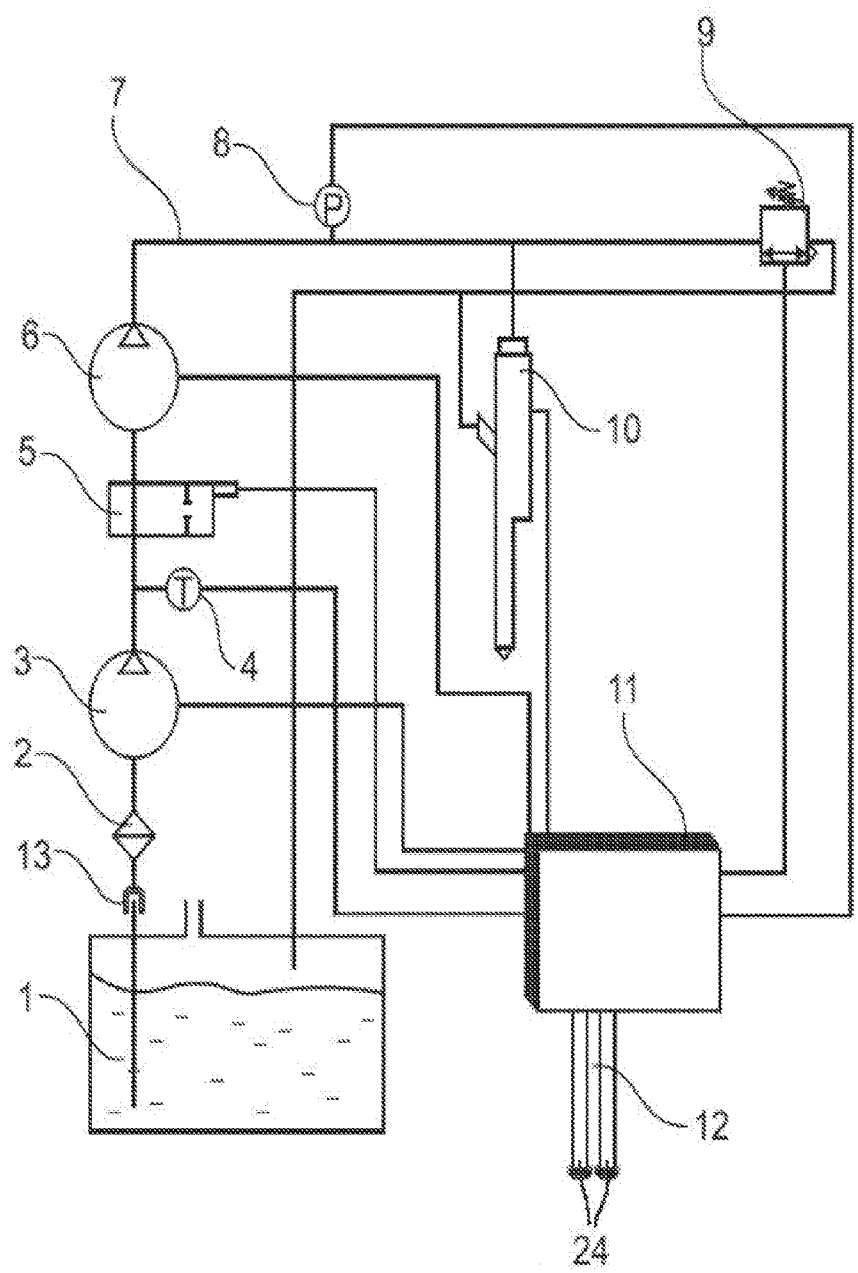
FIG. 1 shows a device for placing media into or underneath the skin.

FIG. 1 shows possible components of a device for placing media into or underneath the skin:
  1 Reservoir for the media to be placed
  2 Filter
  3 Pre-supply pump
  4 Temperature sensor for temperature-sensitive media
  5 Pressure control valve
  6 High-pressure pump
  7 Pressure reservoir
  8 Manometer
  9 Pressure limiter with return line to the reservoir
  10 Applicator unit
  11 Electronic control unit
  12 Lines for the hand and/or foot control unit
  13 Quick coupling An exemplary working method of the device for placing media into or underneath the skin is described in the following in conjunction with FIG. 1. A pre-supply pump 3 sucks a medium from a reservoir 1 via a filter 2 and supplies the medium, under pressure, into a high-pressure pump 6. The high-pressure pump 6 is preferably a radial piston pump driven with an electric motor with a pressure and quantity control. A temperature sensor 4 can monitor the temperature of the medium and can provide a warning when adjustable temperature limits are exceeded for temperature-sensitive media. A pressure control valve 5 controls the inflow pressure to the electronically controlled high-pressure pump 6. This high-pressure pump 6 pumps the medium into a pressure reservoir 7 in the form of a hose that is configured to smooth the oscillations or equalize the pressure, which preferably serves as a supply hose for feeding the medium into a spatially separated injection nozzle on an applicator unit 10. An upstream manometer 8 provides the pressure signal for controlling the high-pressure pump 6 to the electronic control unit 11. The device can further comprise an additional pressure limiter 9 with a return line to the reservoir 1. The electronic control unit 11 comprises the electric power-supply for the device and the lines for the handheld control unit. The electronic control unit 11 can consequently adjust to any constant starting pressure due to the control of the high-pressure pump 6 and/or the pressure control valve 5 or the pressure limiter 9 and can define the series of pressure pulses in relation to the amount and frequency of injection pulses due to the control of the applicator unit 10. A quick coupling 13 can enable easy coupling of various reservoirs 1 to allow use of other media and a suitable rinsing fluid.

In other words, the exemplary device for providing media into or underneath the skin comprises a reservoir 1 for providing media, a control unit 11, and an applicator unit 10, which are connected to one another through a hose system or an electric cable. This enables an ergonomic design of the applicator unit 10, for example in the shape of a ballpoint pen. The applicator unit 10 can also have the shape of an endoscopic device in order to supply media, for example, into the lining of the stomach.

Figure 2:
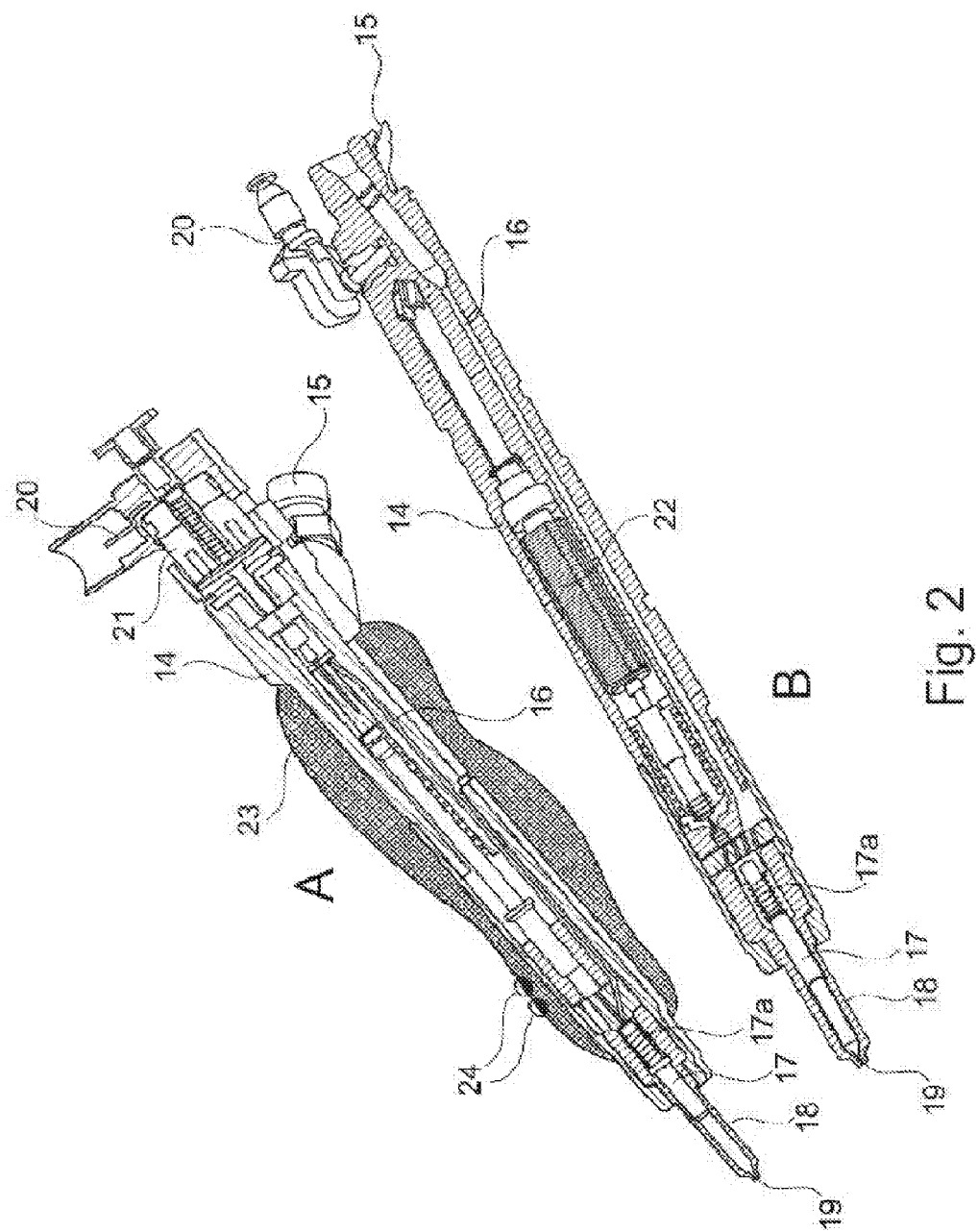
FIG. 2 shows an applicator unit for the device for placing media into or underneath the skin.

FIG. 2 shows possible components of an applicator unit for the device for placing media into or underneath the skin:
- 14 Housing
- 15 Media supply
- 16 Internal media channel
- 17 Nozzle needle
- 17a Spring
- 18 Nozzle head
- 19 Nozzle tip with exit holes (orifice)
- 20 Connection for electric control line
- 21 Solenoid
- 22 Piezo unit
- 23 Handle
- 24 Control buttons An exemplary working method of the applicator unit for the device for placing media into or underneath the skin is described in the following in conjunction with FIG. 2. A housing 14 is preferably surrounded by an anatomically shaped hand grip into which control buttons 24 are integrated for pressure and frequency. The housing 14 further contains connections for media supply 15 through pressure lines. The liquid reaches a preferably replaceable nozzle head 18 having at least one injection nozzle via an internal media channel 16. From there, a nozzle needle 17, loaded by the closing force of a spring 17a, seals off the exit holes in the nozzle tip 19. Via electrical connections 20, a solenoid 21 or a piezo unit 22, for example, receives an electric pulse and relaxes the force on the nozzle needle 17, which lifts up and releases the exit holes.

The injection nozzle with the spring-loaded nozzle needle 17 is controlled by the electronic control unit 11 and can function purely mechanically/hydraulically, or is electrically controlled with a solenoid (see variant A in FIG. 2) or with piezo-electrical actuation (see variant B in FIG. 2). In other embodiments, approaches to the injection process are also possible using hydraulic amplification or pressure generation piezo-electric modules in the applicator unit 10. The advantages of this type of operation can be found in the potentially high limit frequency and the fine modulation of the pressure patterns during the injection process that enable the least possible amount of lesions when penetrating the respective skin type. In other words, the pressure and/or the acceleration of the medium as well as the medium quantity are variable and can be precisely adjusted via the electric control unit 11. The distribution of the medium with respect to droplet and/or particle size and jet emission angle can be determined by the design of a downstream nozzle. The dispensing of the medium can take place in individual pulses or in a series of pulses with controllable frequencies in a broad frequency band.

After activation of the actuating buttons 24, the operator moves slowly with the applicator unit 10 over the tissue to be treated. Depending on need, the applicator unit 10 can be placed on the skin to be treated or positioned manually or with a suitable device within an adjustable distance above the skin. Depending on the quantity of transdermal media to be supplied, the frequency and movement speed as well as the selected nozzle head 18 must be coordinated. The desired penetration depth can be determined with the pressure control and the respective nozzle head 18.

By varying the injection pressure, the penetration depth into the tissue can be regulated while the injection frequency and the selected nozzle unit determine the quantity to be supplied per surface area with the selected movement speed of the applicator unit over the treated surface. Thus, the operator can control the desired penetration depth and quantity of the medium into or underneath the skin via the injection frequency and the selection of the nozzle head 18 with various nozzle holes and the penetration depth of the medium during application via the pressure control.

Figure 3:
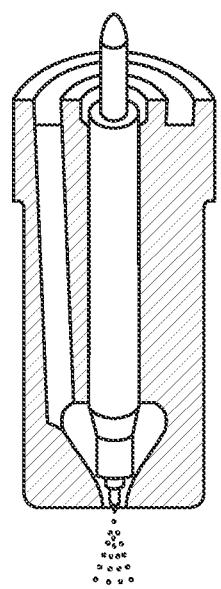
FIGS. 3 and 4 show various injection nozzles for the device for placing media into or underneath the skin.
Figure 4:
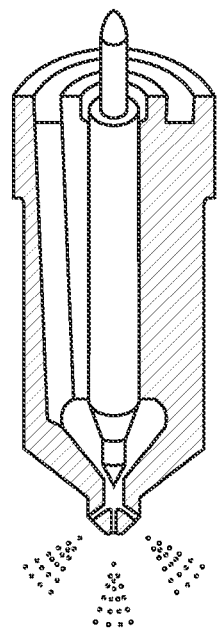

Depending on the selected nozzle head 18, the injection stream can be tightly or broadly concentrated, i.e. can be a thin stream or a cone-shaped spray in the micrometer range. The selection of the replaceable nozzle head 18 also determines how the media will be supplied (intradermal/intramucosal, or transdermal/transmucosal). Pin nozzles (see FIG. 3) concentrate the injection stream such that the maximum depth of penetration is achieved. They can form a cylindrical injection stream or a stream expanded as a taper. Multi hole-type nozzles (see FIG. 4) having, for example, up to 12 exit holes, on the other hand, will achieve a very broad distribution of the medium. The diameter of the nozzle holes determines the properties and/or the quality of the injection as a further parameter. The embodiment having a thin stream is preferred if the active ingredient is supposed to be applied into tissue that is very deep, for example into the musculature (botulinum toxin A). The embodiment having a tapered spray is preferred for flat treatment of skin. Thus large areas of skin can be infiltrated with the active ingredient almost pain-free, for example the epidermis or the dermis.

For simple control of the application, the buttons for frequency and pressure are preferably integrated directly on the handle 23 such that one-handed operation is possible. A foot control represents one variant with which the pressure and frequency are combined into one pedal or can be controlled individually. Likewise, a combination between a hand and foot control is possible. The device for supplying media can be disposable or a reusable article that can be re-sterilized.

Depending on the duration of the electrical pulse, the opening duration can be a few milliseconds up to a time-frame of seconds. The prerequisite for a long injection time is a sufficiently dimensioned performance of the high-pressure pump 6. In conjunction with the electric control unit 11, fine regulation of the transdermal injection with separate variation of the injection pressure and injection frequency is enabled.

Depending on the liquid to be injected (corrosive, not lubricating), corrosion-resistant materials or special design details may be necessary.

In order to prevent destruction of long-chain molecules in the media to be supplied, all valves, line connections, and channel lines may be designed with the largest possible radii without sharp edges.

What is claimed is:

1. A system to inject a medium into or underneath the skin with a series of pressure pulses, comprising:
   a reservoir for the medium,
   a hose comprising a pressure reservoir;
   a handheld application unit spatially separated from the reservoir and configured to inject the medium into or underneath the skin via a controllable injection nozzle, comprising:
      a handle having control buttons configured to adjust the injection pressure and the injection frequency of the medium during application of the medium,
      at least one injection nozzle comprising at least one exit hole configured to form a fluid jet, wherein the at least one injection nozzle can be sealed or opened by a movable nozzle needle,
   a hydraulic high-pressure pump configured to receive the medium from the reservoir and pump the medium into the application unit via the hose, wherein the hose connects the reservoir and the application unit,
   an electronic control unit configured to control the application unit and the movable nozzle needle such that the medium is injected into or underneath the skin with a series of pressure pulses, wherein the injection frequency and thus the quantity of the medium injected per unit of time is controllable via the electronic control unit and opening and closing the at least one exit hole in the at least one injection nozzle by the movable nozzle needle, and
   a pressure limiter located fluidically between the application unit and the high-pressure pump, wherein the pressure limiter is controllable by at least one of the control buttons and the electronic control unit to adjust the injection pressure of the medium and thus the injection depth of the medium into or underneath the skin.

2. The system according to claim 1, wherein a line for feeding the medium from the high-pressure pump to the application unit is simultaneously a pressure reservoir.

3. The system according to claim 1, wherein the movable nozzle needle can be mechanically-hydraulically, electro-magnetically, or piezo-electrically operated.

4. The system according to claim 1, wherein the injection nozzle has the shape of a pin nozzle for the maximum depth of injecting or the shape of a hole-type nozzle for the maximum width of injecting the medium into or underneath the skin.

5. The system according to claim 1, wherein the application unit or the injection nozzle is replaceable, such that the quantity of medium per surface area to be applied is controllable via the selection of various application units or various injection nozzles with various diameters.

6. The system according to claim 1, further comprising a quick coupling configured for coupling to the reservoir to allow replacement of the reservoir with one or several additional reservoirs for using various media.

7. The system according to claim 6, wherein the various media comprise a rinsing fluid.

8. The system according to claim 1, wherein the application unit is spatially separated from the reservoir and the high-pressure pump.

9. The system according to claim 1, wherein the pressure limiter and a return line to the reservoir from the pressure limiter are in parallel to the line for feeding the medium from the high-pressure pump to the application unit.

10. The system according to claim 1, further comprising a return line fluidly connecting the application unit to the reservoir.

11. The system according to claim 10, wherein the application unit comprises a replaceable nozzle head.

12. The system according to claim 11, further comprising a pre-supply pump fluidly connecting the reservoir and the hydraulic high-pressure pump.

13. The system according to claim 12, wherein the handle does not contain the reservoir, hydraulic high-pressure pump, and the hose comprising the pressure reservoir.

\* \* \* \* \*